United States Patent
De Wet et al.

(10) Patent No.: US 6,479,722 B1
(45) Date of Patent: Nov. 12, 2002

(54) PRODUCTION OF DIMERS

(75) Inventors: Hester De Wet; David Hedley Morgan; Alta Ranwell, all of Vanderbijlpark (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 0 days.

(21) Appl. No.: 09/673,267

(22) PCT Filed: Apr. 26, 1999

(86) PCT No.: PCT/IB99/00747
§ 371 (c)(1),
(2), (4) Date: Nov. 1, 2001

(87) PCT Pub. No.: WO99/55646
PCT Pub. Date: Nov. 4, 1999

(30) Foreign Application Priority Data

Apr. 28, 1998 (ZA) ................................. 98/3539

(51) Int. Cl.$^7$ ............................. C07C 2/26; C07C 2/24; C07C 2/02
(52) U.S. Cl. ........................ 585/511; 585/512; 585/523; 585/524
(58) Field of Search ................................ 585/511, 512, 585/523, 524

(56) References Cited

U.S. PATENT DOCUMENTS 4,513,156 A    4/1985    Tabak ........................ 585/329
4,658,078 A  *  4/1987    Slaugh et al.

FOREIGN PATENT DOCUMENTS

| WO | 9215541 | 9/1992 |
|----|---------|--------|
| WO | 9852888 | 11/1998 |

* cited by examiner

*Primary Examiner*—Hien Tran
*Assistant Examiner*—Tam M. Nguyen
(74) *Attorney, Agent, or Firm*—Ladas & Parry

(57) ABSTRACT

A process for the production of dimers from an olefinic feedstock containing α-olefins, by contacting the feedstock with a metallocene/aluminoxane catalyst, thereby selectively to dimerize α-olefins in the feedstock by way of a metallocene-catalyzed dimerization reaction. The feedstock is in the form of a Fischer-Tropsch-derived olefinic feedstock involving a mixture of Fischer-Tropsch-derived hydrocarbons made up of at most 90% by mass of α-olefins, at least 5% by mass of olefins, other than α-olefins, selected from linear internal olefins, branched internal olefins, cyclic olefins, dienes, trienes and mixtures thereof, at least 5% by mass of constituents, other than olefins, selected from paraffins, oxygenated hydrocarbons, aromatic hydrocarbons and mixtures thereof. The metallocene-catalyzed dimerization reaction takes place while the olefins which are dimerized form part of the mixture constituted by the feedstock.

10 Claims, No Drawings

PRODUCTION OF DIMERS

THIS INVENTION relates to a process for the production of dimers from an olefinic feedstock. More particularly, the invention relates to a process suitable for the production of a product having the general formula R'R"C=$CH_2$, in which R' and R" are alkyl groups, from an olefinic feedstock.

According to the invention there is provided a process for the production of dimers from an olefinic feedstock containing α-olefins, the process comprising contacting the feedstock with a metallocene/ aluminoxane catalyst, thereby selectively to dimerize α-olefins in the feedstock by means of a metallocene-catalyzed dimerization reaction, the feedstock being in the form of a Fischer-Tropsch-derived olefinic feedstock comprising a mixture of Fischer-Tropsch-derived hydrocarbons made up of at most 90% by mass of α-olefins, at least 5% by mass of olefins, other than α-olefins, selected from linear internal olefins, branched internal olefins, cyclic olefins, dienes, trienes and mixtures thereof, and at least 5% by mass of constituents, other than olefins, selected from paraffins, oxygenated hydrocarbons, aromatic hydrocarbons and mixtures thereof, the metallocene-catalyzed dimerization reaction taking place while the olefins which are dimerized form part of the mixture constituted by the feedstock.

By a Fischer-Tropsch-derived olefinic feedstock is meant an olefinic feedstock which is a product obtained by subjecting a synthesis gas comprising carbon monoxide and hydrogen to Fisher-Tropsch reaction conditions in the presence of a suitable Fischer-Tropsch catalyst, which catalyst may be iron-based, cobalt-based or iron/cobalt-based. In particular the Fischer-Tropsch-derived olefinic feedstock may be one which, after production thereof from the synthesis gas, has been subjected to no substantial further treatment, purification or processing thereof to remove unwanted constituents such as non-α-olefins therefrom, other than cutting so that a suitable cut of the Fischer-Tropsch-derived product will typically be selected for use as the feedstock.

The feedstock may comprise 50–90% by mass of said α-olefins, for example 60–80% by mass thereof; it may comprise 5–20% by mass of said olefins other than α-olefins, for example 9–16% by mass thereof; and it may comprise 5–30% by mass of said constituents other than olefins, for example 13–22% by mass thereof.

By way of example, the feedstock may comprise 50% by mass of α-olefins, 20% by mass olefins other than α-olefins, and 30% by mass of constituents other than olefins. The metallocene/aluminoxane catalyst may have an aluminoxane component which is methylaluminoxane, and a metallocene component which is a compound of the general formula $(Cp)_2MY_2$ in which Cp represents a cyclopentadienyl group, M is a metal selected from zirconium, hafnium and titanium, and Y is selected from hydrogen radicals, halogen radicals (preferably chlorine radicals), alkyl groups (preferably methyl groups) and mixtures thereof. The metallocene component preferably comprises a single compound of said formula $(Cp)_2MY_2$, but it may instead comprise a mixture of several said compounds of formula $(Cp)_2MY_2$.

Still more particularly, the feedstock may comprise olefins other than α-olefins which include linear and/or branched internal olefins, cyclic olefins, dienes and trienes, and constituents of the feedstock other than olefins may include paraffins, aromatics and small amounts of oxygenates. There may be an Al:M atomic ratio between aluminium in the aluminoxane component of the catalyst and the metal M in the metallocene component of the catalyst of 1:1–100:1, preferably 40:1–80:1, eg 60:1–70:1, As the Al:M atomic ratio increases, the degree of conversion and reaction rate increase, while the selectivity with regard to dimer production decreases, while a reducing Al:M atomic ratio reduces the degree of conversion and the reaction rate, and increases the selectivity for dimer production. An optimum or acceptable Al:M atomic ratio may accordingly be selected by routine experimentation, bearing practical and economic considerations in mind.

It is preferred to have the feedstock in a liquid state during the contacting of the catalyst with the feedstock, and the contacting may take place at a reaction temperature, and at a reaction pressure, both of which can vary within broad limits, the reaction time being determined by the period required to obtain a desired degree of conversion. Thus, reaction temperatures of −60° C. to 280° C., eg 20–120° C. have been found to be suitable, and absolute reaction pressures of 1 atmosphere or less, up to 500 atmospheres or more, may be used. In a particular case, the feedstock may be in a liquid state during the contacting of the feedstock with the metallocene/aluminoxane catalyst, the contacting taking place at a reaction temperature of −60° C. to 280° C. and at an absolute reaction pressure of 1–500 atmospheres, usually at or slightly above 1 atmosphere; and in this case the reaction temperature if preferably 20–120° C., the process being carried out under an inert atmosphere. Once again, routine experimentation may be used to establish optimum or acceptable reaction conditions with regard to temperature, pressure and reaction time.

In accordance with the process of the present invention the aluminoxane component of the catalyst, dissolved in an organic solvent (conveniently the organic solvent used in the preparation of the aluminoxane component) may be admixed with a well-stirred suspension of the metallocene component of the catalyst in an organic liquid which may be inert with regard to the metallocene/aluminoxane catalyst, or conveniently may be in the form of the feedstock used for the dimerization reaction. When the feedstock is used to suspend the metallocene component, the dimerization reaction proceeds in earnest as soon as the admixture thereof with the aluminoxane solution becomes substantially homogeneous. The dimerization is conveniently carried out under an inert atmosphere, eg an argon atmosphere, at atmospheric pressure.

The invention will now be described, by way of non-limiting illustration, with reference to the following Examples:

EXAMPLE 1

A metallocene/aluminoxane catalyst was prepared by admixing 3.07 g of a 30% by mass methylaluminoxane solution in toluene with 0.24 g of $(Cp)_2ZrCl_2$ (zirconocene dichloride) with stirring at room temperature for about 15 minutes under argon, that catalyst having an Al:Zr atomic ratio of 66:1.

31.89 g of a Fischer-Tropsch-derived $C_7$ cut (containing about 74% by mass of 1-heptene) and 44.82 g of a Fischer-Tropsch-derived $C_9$ cut (containing about 65% by mass of 1-nonene) were admixed with the catalyst under argon in a reaction vessel in the form of a 300 ml flamed-out Schlenk flask, followed by stirring at room temperature and atmospheric pressure under argon for about 4 hours, before being quenched with a 10% by mass solution of hydrochloric acid in methanol. The quenched solution was stirred for a further 30 minutes and was then washed with water and concentrated with regard to dimer reaction product. Gas-chromatographic analysis of the concentrated washed product showed a degree of conversion of >85% and a mole ratio of dimerization and cross-dimerization products of $C_{14}:C_{16}:C_{18}$ of 1:2:1 where $C_{14}$ represents the dimerization product of two of the heptene molecules, $C_{18}$ represents that of two of the nonene molecules, and $C_{16}$ represents the cross-dimerization product of one of the heptene molecules with one of the nonene molecules.

EXAMPLE 2

Example 1 was repeated using 3.552 g of the methylaluminoxane and 0.22 g of the $(Cp)_2ZrCl_2$, with 79.19 of a Fischer-Tropsch-derived $C_8$ cut (containing about 40% by mass of 1-octene). The gas-chromatographic analysis showed that the degree of conversion to a $C_{16}$ product was >77%.

An advantage of the invention is that the Applicant has discovered that, surprisingly, a high degree of α-olefinic feedstock purity is not required for an-effective dimerization. Instead, a Fischer-Tropsch-derived olefinic feedstock containing substantial proportions of non-α-olefinic constituents may be employed without any substantial treatment, purification or processing thereof, other than the selection of a suitable cut or cuts thereof containing α-olefins predominantly of the desired number or numbers of carbon atoms, to produce dimers of the desired number or numbers of carbon atoms. The dimers in question can be represented by $R'R''=CH_2$ in which R' and R'' are alkyl groups and may be the same of different, the dimer being formed from the α-olefins $R'=CH_2$ and $R''=CH_2$, R' and R'' each having typically $C_2$–$C_{30}$ carbon atoms, preferably $C_5$–$C_{10}$ carbon atoms.

The dimer reaction products of the process of the present invention are useful as starting materials for the production, eg by hydroformylation, of oxygenated products such as aldehydes or alcohols, which in turn can be used to make detergents, surfactants or the like.

While the invention is expected to be suitable for use with any Fischer-Tropsch-derived olefinic feedstock, it is expected to be particularly suitable for such feedstock when derived from a high temperature Fischer-Tropsch process carried out at a temperature above 280° C., preferably above 300° C., for example at 330° C., as contrasted with feedstocks derived from low temperature Fischer-Tropsch processes, typically carried out at about 220° C.

What is claimed is:

1. A process for the production of dimers from an olefinic feedstock containing α-olefins, the process comprising contacting the feedstock with a metallocene/aluminoxane catalyst comprising a metallocene component and an aluminoxane component, thereby selectively to dimerize α-olefins in the feedstock by means of a metallocene-catalyzed dimerization reaction, the process being characterized in that the olefinic feedstock is in the form of a Fischer-Tropsch-derived olefinic feedstock comprising a mixture of Fischer-Tropsch-derived hydrocarbons made up of at most 90% by mass of α-olefins, at least 5% by mass of olefins, other than a olefins, selected from linear internal olefins, branched internal olefins, cyclic olefins, dienes, trienes and mixtures thereof, and at least 5% by mass of constituents, other than olefins, selected from paraffins, oxygenated hydrocarbons, aromatic hydrocarbons and mixtures thereof, the metallocene-catalyzed dimerization reaction taking place while the olefins which are dimerized form part of the mixture constituted by the olefinic feedstock.

2. A process as claimed in claim 1, characterized in that the feedstock comprises 50–90% by mass of said α-olefins.

3. A process as claimed in claim 1, characterized in that the feedstock comprises 5–20% by mass of said olefins other than α-olefins.

4. A process as claimed in claims 1, characterized in that the feedstock comprises 5–30% by mass of said constituents other than olefins.

5. A process as claimed in claim 1, characterized in that the aluminoxane component is methylaluminoxane, and the metalocene component is a compound of the general formula $(Cp)_2MY_2$ in which Cp represents a cyclopentadienyl group, M is ametal selected from zirconium, hafnium and titanium, and Y is selected from hydrogen radicals, halogen radicals, alkyl groups and mixtures thereof.

6. A process as claimed in claim 5, characterized in that the metallocene component comprises a single compound of said formula $(Cp)_2MY_2$.

7. A process as claimed in claim 5, characterized in that there is an Al:M atomic ratio between aluminium in the aluminoxane component of the catalyst and the metal M in the metallocene component of the catalyst of 1:1–100:1.

8. A process as claimed in claim 1, characterized in that the feedstock is in a liquid state during the contacting of the feedstock with the metallocene/aluminoxane catalyst, the contacting taking place at a reaction temperature of −60° C. to 280° C. and at an absolute reaction pressure of 1–500 atmospheres.

9. A process as claimed in claim 8, characterized in that the reaction temperature is 20–120° C., the process being carried out under an inert atmosphere.

10. A process for the production of dimers consisting essentially of the following steps:
(a) subjecting a synthesis gas comprising carbon monoxide and hydrogen to Fischer-Tropsch reaction conditions in the presence of a Fischer-Tropsch catalyst to produce an olefinic feedstock comprising a mixture of Fischer-Tropsch-derived hydrocarbons made up of at most 90% by mass of α-olefins, at least 5% by mass of olefins other than α-olefins selected from the group consisting of linear internal olefins, branched internal olefins, cyclic olefins, dienes, trienes and mixtures thereof, and at least 5% by mass of constituents, other than olefins, selected from the group consisting of paraffins, oxygenated hydrocarbons, aromatic hydrocarbons and mixtures thereof;
(b) recovering the olefinic feedstock; and
(c) selectively dimerizing α-olefins in the olefinic feedstock recovered in step (b) in a metallocene-catalyzed dimerization reaction by contacting the olefinic feedstock with a catalyst comprising a metallocene component and an aluminoxane component, the metallocene-catalyzed dimerization reaction taking place while the olefins which are dimerized form part of the mixture constituted by the olefinic feedstock.

* * * * *

UNITED STATES PATENT AND TRADEMARK OFFICE
CERTIFICATE OF CORRECTION

PATENT NO.   : 6,479,722 B1
DATED        : November 12, 2002
INVENTOR(S)  : Hester De Wet et al.

It is certified that error appears in the above-identified patent and that said Letters Patent is hereby corrected as shown below:

<u>Title page,</u>
Item [86], "2001" should read -- 2000 --.

Signed and Sealed this

Twenty-fifth Day of February, 2003

JAMES E. ROGAN
*Director of the United States Patent and Trademark Office*